US010470690B2

(12) United States Patent
Hasegawa et al.

(10) Patent No.: US 10,470,690 B2
(45) Date of Patent: Nov. 12, 2019

(54) AUTHENTICATION DEVICE USING BRAINWAVES, AUTHENTICATION METHOD, AUTHENTICATION SYSTEM, AND PROGRAM

(71) Applicant: National Institute of Advanced Industrial Science and Technology, Tokyo (JP)

(72) Inventors: Ryohei Hasegawa, Ibaraki (JP); Yukako Hasegawa, Ibaraki (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 201 days.

(21) Appl. No.: 15/527,387

(22) PCT Filed: Nov. 17, 2015

(86) PCT No.: PCT/JP2015/082178
§ 371 (c)(1),
(2) Date: Jul. 13, 2017

(87) PCT Pub. No.: WO2016/080366
PCT Pub. Date: May 26, 2016

(65) Prior Publication Data
US 2017/0325720 A1    Nov. 16, 2017

(30) Foreign Application Priority Data
Nov. 21, 2014    (JP) .................................. 2014-236574

(51) Int. Cl.
*A61B 5/117*    (2016.01)
*A61B 5/0476*   (2006.01)
(Continued)

(52) U.S. Cl.
CPC ............ *A61B 5/117* (2013.01); *A61B 5/0476* (2013.01); *A61B 5/04842* (2013.01); *A61B 5/6814* (2013.01); *A61B 5/04012* (2013.01)

(58) Field of Classification Search
None
See application file for complete search history.

(56) References Cited

U.S. PATENT DOCUMENTS 5,467,777 A * 11/1995 Farwell ............... A61B 5/0478
600/544
2002/0188217 A1* 12/2002 Farwell ................. A61B 5/164
600/544
(Continued)

FOREIGN PATENT DOCUMENTS

CN    101558997 A  * 10/2009
JP    201253656 A    0/3201
(Continued)

OTHER PUBLICATIONS

International Search Report, PCT/JP2015/082178, dated Feb. 8, 2016, pp. 2.
(Continued)

*Primary Examiner* — Jiangeng Sun
(74) *Attorney, Agent, or Firm* — Cantor Colburn LLP (57) ABSTRACT

Provided are a highly confidential personal authentication device which uses brain waves, a personal authentication method, and a personal authentication system and program. The authentication device using brain waves is provided with: an electroencephalograph; and a processing unit which, with respect to brain waves with respect to a plurality of stimulus events obtained by the electroencephalograph, determines a discrimination score according to a discrimination model for estimating brain information for each authentication candidate accumulated in advance, based on a discrimination-model-to-discrimination-model compari-
(Continued)

son of the discrimination score, identifies and authenticates an authentication candidate who provided the model. The identifying of the authentication candidate based on the discrimination score in the processing unit is based on the discrimination score and/or decoding accuracy determined from the discrimination score.

11 Claims, 6 Drawing Sheets

(51) Int. Cl.
    *A61B 5/00*     (2006.01)
    *A61B 5/0484*     (2006.01)
    *A61B 5/04*     (2006.01)

(56) References Cited

U.S. PATENT DOCUMENTS

2014/0020089 A1* 1/2014 Perini, II ............... G06F 21/32
                                                              726/19

2016/0103487 A1* 4/2016 Crawford ............... G06F 3/015
                                                              600/544

FOREIGN PATENT DOCUMENTS

| JP | 2004248714 A | 9/2004 |
|---|---|---|
| JP | 2005293209 A | 10/2005 |
| JP | 2010274035 A | 12/2010 |
| JP | 201253656 A | 3/2012 |
| JP | 201273329 A | 4/2012 |
| JP | 2013178601 A | 9/2013 |

OTHER PUBLICATIONS

Ryohei P. Hasegawa et al., "Single trial-based prediction of a go/no-go decision in monkey superior colliculus", Available online at www.sciencedirect.com, Neural Networks 19 (2006) 1223-1232.
Hasegawa, et al., "Developmment of Neuroauthenticator: Feasibility of an EEG-based authentication," 2017 International Conference on Biometrics and Kansei Engineering: IEEE; pp. 127-131.

* cited by examiner

AUTHENTICATION DEVICE USING BRAINWAVES, AUTHENTICATION METHOD, AUTHENTICATION SYSTEM, AND PROGRAM

TECHNICAL FIELD

The present invention relates to biometric authentication using brain waves, and relates to an authentication device, an authentication method, an authentication system, and a program which use brain waves.

BACKGROUND ART

In recent years, personal authentication technologies using passwords and items (such as IC cards) have become generally widespread as a main pillar of information security. With these authentication technologies, however, the user may fail to authenticate themselves if they forget the password or lose the item. The technologies are also subject to leakage or theft, which may lead to authentication of other people. In contrast, authentication using biometric information is considered to be less likely to suffer from such risk. Biometric information eliminates the need for key inputs or carrying the item. Accordingly, biometric information provides an easy-to-use means of authentication, and is believed to be able to prevent authentication of a third party other than the right person. Examples of biometric authentication include fingerprints and the iris of the eye. Vein authentication, which reads the shape of blood vessels in the palm or finger, is being utilized at the bank ATMs, for example. Other authentication techniques using voiceprint, facial shape, handwriting and the like have also been put to practical use. However, even biometric authentication is subject to the potential of being breached by copying.

Meanwhile, various researches on the relationship between the human thought and behavior and the brain activity have been conducted over the years. Brain-Machine Interface (BMI) technology for controlling an external device or transmitting an intension to the others by focusing on biometric signals of brain activities, for example, is gaining attention.

The present inventors have proposed a virtual decision function and indicated a computation method therefor (see Non Patent Literature 1). Non Patent Literature 1 discloses an either-or behavior prediction method based on neural activity, taking a single neuron activity as an example.

The present inventors have also proposed an intension transmission assistance device and method for transmitting intensions by analyzing brain activity (see Patent Literatures 1 and 2). The techniques disclosed in Patent Literatures 1 and 2 make it possible to, for example, assist transmission of intensions of a motion-impaired person having difficulty speaking or writing, or a motion-impaired person having difficulty making input operations on various devices using hands or legs.

The present inventors have also proposed a technique for providing a map-like representation of in-brain information expressions using brain wave analysis for general subjects including able-bodied persons (see Patent Literature 3). The present inventors have also proposed a device and method for ordering, by brain wave analysis, objects to be investigated (see Patent Literature 4).

A prior art search has identified proposed authentication methods which utilize brain waves (see Patent Literatures 5 and 6). Patent Literature 5 proposes personal authentication based on the distance between a base based on an object person's brain waves and a base based on an object person candidate's brain waves, the bases being frequency components acquired from brain waves by Fourier transform, or time-domain components acquired from brain waves by correlation dimension analysis. Patent Literature 6 proposes a personal authentication method which, in addition to the verification of identity by existing biometrics authentication, detects when the valid user is forced to carry out an unauthorized operation. The method utilizes, for determining psychological states, information about brain waves, heart rates, amount of perspiration and the like as biometric information indicative of emotional features.

CITATION LIST

Patent Literature

Patent Literature 1: JP 2012-053656 A
Patent Literature 2: JP 2012-073329 A
Patent Literature 3: JP 2010-274035 A
Patent Literature 4: JP 2013-178601 A
Patent Literature 5: JP 2004-248714 A
Patent Literature 6: JP 2005-293209 A

Non Patent Literature

Non Patent Literature 1: R. Hasegawa, et al., "Single trial-based prediction of a go/no-go decision in monkey superior colliculus", Neural Networks 19 (2006) 1223-1232

SUMMARY OF INVENTION

Technical Problem

The prior art according to Patent Literatures 1 and 2 had the object of enabling high-speed and high-accuracy decoding of decisions in the brain by analyzing brain wave data.

The technique the present inventors have proposed in Patent Literature 1 will be described in detail.

Patent Literature 1 is directed to a technique for solving the problem that the devices that had been proposed earlier by researches concerning intension transmission have large noise, suffer from a low probability of correct answers, and take a long determination time, making the devices unsuitable for measuring biometric information such as brain waves. In particular, the technique according to Patent Literature 1 makes it possible to distinguish intensions in the brain without an erroneous determination and in a short time, directly operate a device by thoughts in the brain of an operator in real time, and for a patient or an elderly with speech impediment to more simply and directly communicate his or her intensions concerning basic personal care, feelings and the like to helpers.

The technique according to Patent Literature 1 is based on a "virtual decision function", which is a technique for quantifying in-brain processes of making a decision that the present inventors had previously been researching and developing. In Patent Literature 1, the concept of the virtual decision function is greatly expanded so as to be utilized as an in-brain intension decoding technique for an intension transmission device based on brain wave measurement. Patent Literature 1 also proposes a technique whereby brain wave decoding is interrupted and an answer is given when the prediction probability is sufficiently increased.

The intension transmission assistance device according to Patent Literature 1 includes a stimulus presentation device, and a processing device which processes brain wave data from an electroencephalograph which measures brain waves after the stimulus presentation by the stimulus presentation device. The intension transmission assistance device is characterized in that the processing device determines that a specific decision has been made in the brain based on a discrimination function obtained by analyzing the brain wave data and a success rate. Based on the product of an accumulated discrimination score by the discrimination function obtained by analyzing the brain wave data and the success rate, it is determined that a specific decision has been made in the brain when the product has exceeded a threshold value, and the determination result is output to a device. Patent Literature 1 indicates that the function obtained by analyzing the data measured by the electroencephalograph is a multivariate analysis function, such as a logistics function or a linear discrimination analysis function, and that weighting of variables is set for each channel of the brain waves and after the elapse of a certain time after stimulus presentation.

The technique disclosed in Patent Literature 1 makes it possible to decode an intension in the brain in real-time, and assist transmission of the intension, where the success rate is used as a numerical value for creating an improved virtual decision function. The devices disclosed in Patent Literatures 1 and 2 are based on a real-time decoding of an event-related potential (ERP), among other brain waves reflecting various brain information, which is related to the cognitive function in particular.

The patterns of the event-related potential on which many brain-wave BMI techniques, including the intension transmission assistance devices of Patent Literatures 1 and 2, focus attention have large individual differences. Accordingly, the techniques are difficult to be adapted for general purposes, particularly in terms of practical application as an intension transmission device for persons with disabilities. The difficulty of adaptation for general purposes lies in that a brain-wave discrimination model formula trained with one person's brain wave pattern does not provide sufficient decoding accuracy for another person. That is, the brain wave pattern of each person needs to be registered. This disadvantage as a welfare device, on the other hand, may prove to be an advantage for an information security device, because this means that only the particular individual for whom the control of an external device (such as "login to a system" or "open a door") is permitted can perform the control.

A personal authentication system is also known which is based on individual differences in the brain wave pattern of event-related potentials during the execution of an "oddball" task (which triggers a bottom-up increase in attention with respect to a stimulus that appears only rarely among a number of identical stimuli). However, in terms of construction of a practical brain wave authentication system, the oddball task, in which the stimulus that triggers an event-related potential is knowable by anyone, is risky, and the authentication accuracy is low at approximately 90%.

The present invention was made with a view to solving the above problems, and an object of the present invention is to provide a personal authentication device, a personal authentication method, a system, and a program for personal authentication with high level of confidentiality and high authentication accuracy.

Solution to Problem

In order to achieve the object, the present invention includes the following features.

The present invention provides an authentication device using brain waves, the device including an electroencephalograph; and a processing unit which, with respect to brain waves obtained by the electroencephalograph with respect to a plurality of stimulus events, determines a discrimination score according to a discrimination model for estimating brain information for each authentication candidate accumulated in advance, and which, based on a discrimination-model-to-discrimination-model comparison of the discrimination score, identifies and authenticates an authentication candidate who provided the model. The identifying of the authentication candidate based on the discrimination-model-to-discrimination-model comparison in the processing unit may be based on the discrimination score and/or a decoding accuracy determined from the discrimination score. The brain waves may be brain waves related to a cognitive process with respect to the stimulus events. The discrimination model for estimating the brain information may have a weighting coefficient therefor optimized so as to enable decoding of a target from the brain waves in a target selection task. The authentication device using brain waves may further include a stimulus presentation unit which presents a plurality of stimulus events, and a target presentation unit which indicates which of the plurality of stimulus events is a target, wherein the brain waves obtained by the electroencephalograph may be brain waves related to a cognitive task for selecting the target. The stimulus presentation unit may present stimulus events having different figures, or stimulus events which only differ in position. The identifying of the authentication candidate based on the discrimination-model-to-discrimination-model comparison by the processing unit may include identifying a highest rank by: a rank, by the discrimination-model-to-discrimination-model comparison, of an average value with respect to a target in standardized data of an accumulated discrimination score with respect to each stimulus type; a rank, by the discrimination-model-to-discrimination-model comparison, of a decoding accuracy determined from the discrimination score; or an average value of ranks of accumulated values of both the discrimination score and the decoding accuracy.

The present invention provides an authentication device using brain waves, the device including an electroencephalograph; and a processing unit which determines decoding accuracy by subjecting brain waves obtained by the electroencephalograph with respect to a plurality of stimulus events to decoding processing according to a decoding model for estimating brain information for each authentication candidate accumulated in advance, and identifies and authenticates an authentication candidate who provided the model formula, based on the decoding accuracy.

The present invention provides an authentication method using brain waves, the method including measuring brain waves of a person to be authenticated which are caused by a plurality of stimulus events; determining, with respect to the brain waves, a discrimination score according to a discrimination model for estimating brain information for each authentication candidate accumulated in advance; and based on a discrimination-model-to-discrimination-model comparison of the discrimination score, identifying and authenticating an authentication candidate who provided the discrimination model.

The present invention provides an authentication system using brain waves, the system including a stimulus presentation device, an electroencephalograph, and a processing device which processes brain wave data from the electroencephalograph. The stimulus presentation device presents a plurality of stimulus events including a target and a non-target, each a plurality of times. The electroencephalograph measures the brain waves of a person to be authenticated which are caused by the plurality of stimulus events. The processing device, with respect to the brain waves, determines a discrimination score according to a discrimination model for estimating brain information for each authentication candidate accumulated in advance, and, based on the discrimination score, identifies and authenticates an authentication candidate who provided the model.

The present invention provides a program for causing a computer to function as a stimulus presentation means which presents a plurality of stimulus events, each a plurality of times; a processing means which, with respect to brain wave data immediately after the stimulus presentation, determines a discrimination score according to a discrimination model for estimating brain information for each authentication candidate accumulated in advance, and, based on the discrimination score, identifies and authenticates an authentication candidate who provided the model; and a presenting means which presents an authentication result.

Advantageous Effects of Invention

According to the present invention, confidential and highly reliable authentication can be performed by analyzing brain waves.

According to the present invention, an authentication accuracy of 95 percent, which conventional authentication using brain waves has been unable to achieve, can be achieved in a short time (five blocks). A further increase in accuracy can be achieved by using various stimulus types, a figure discrimination behavioral task, or a position discrimination task in combinations as appropriate.

According to the present invention, a person to be authenticated or an authentication candidate need not store a password, which makes the present invention effective not only to an able-bodied person but also a person with motor disabilities, for example. Because the authentication uses brain waves, there is no risk of copying.

DESCRIPTION OF EMBODIMENTS

Embodiments of the present invention will be described.

The present invention relates to biometric authentication based on brain wave analysis, and provides a personal authentication technique which enables personal identification only using brain waves.

The present invention focuses on brain activity, particularly event-related potentials, which are a type of brain waves recorded on the scalp, and performs personal identification by analyzing the reactivity of the brain with respect to presentation of a stimulus event. Specifically, the present invention mainly includes the elements of stimulus event presentation, brain wave measurement, brain wave data analysis, personal identification, and identification result presentation.

A device according to the present invention is provided with a headgear for brain wave measurement; a computer for experiment control and data analysis; and a sub-monitor for the subject (display screen (for stimulus presentation)).

Figure 1:
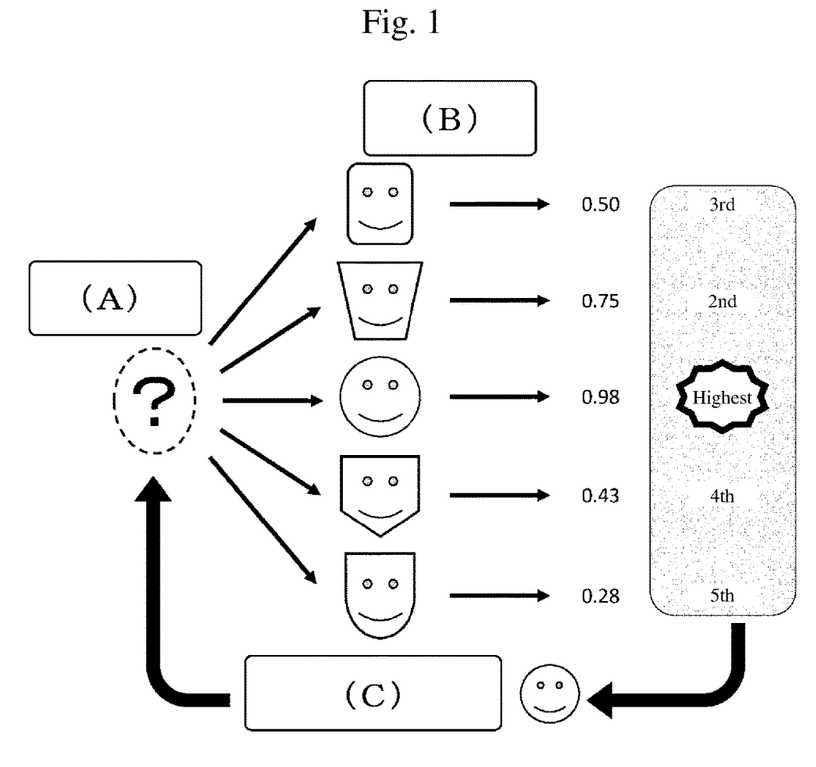
FIG. 1 illustrates the concept of personal identification by brain wave decoding according to the present invention.

FIG. 1 is a schematic diagram illustrating personal identification by brain wave decoding for personal authentication method according to the present invention. In the present invention, as illustrated in FIG. 1, personal authentication by brain waves is performed in the following steps (A), (B), and (C):

(A) Measure brain waves of a person with unknown ID.
(B) Using discrimination models for individual persons that have been registered in a database by prior registration, calculate discrimination scores or, by further advancing the decoding process, decoding accuracy.
(C) Based on the discrimination scores and/or the decoding accuracy, identify the person who provided the highest model.

FIG. 1 will be described in greater detail. The question mark indicates that the person to be authenticated is a person with unknown ID. The faces with different outlines indicate the persons registered in a database by prior registration. When decoding accuracy is calculated according to discrimination model formulas (which may also be referred to as discrimination models) for these persons, the decoding accuracy is 0.50, 0.75, 0.98, 0.43, and 0.28. Accordingly, it is determined that the person who provided the model with the highest value of 0.98 (round outline) is the person to be authenticated, and the person is authenticated. As an example of the brain wave decoding model, a 2-class pattern identification model may be used, such as a model formula by linear discrimination analysis, and support vector machine. In the decoding model according to the present invention, these model formulas may be used.

In step (A), for personal authentication, a user (person who is the object of personal authentication) provides brain wave data during the execution of a "target selection task" which requires a cognitive judgement concerning figure discrimination or position discrimination.

Figure 2:
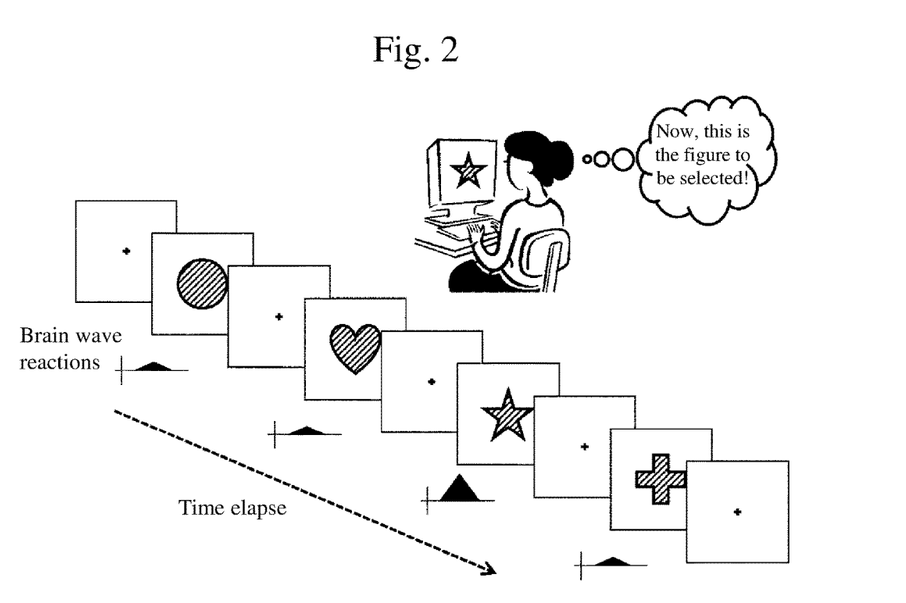
FIG. 2 illustrates an example of figure discrimination in a personal identification behavioral task using brain waves according to the present embodiment.

FIG. 2 illustrates an example of figure discrimination in a personal identification behavioral task using brain waves according to the present embodiment. A target selection task concerning figure discrimination involves merely becoming conscious of a predetermined target when it appeared among a plurality of types of cards with illustrations that are presented in a time series.

Figure 3:
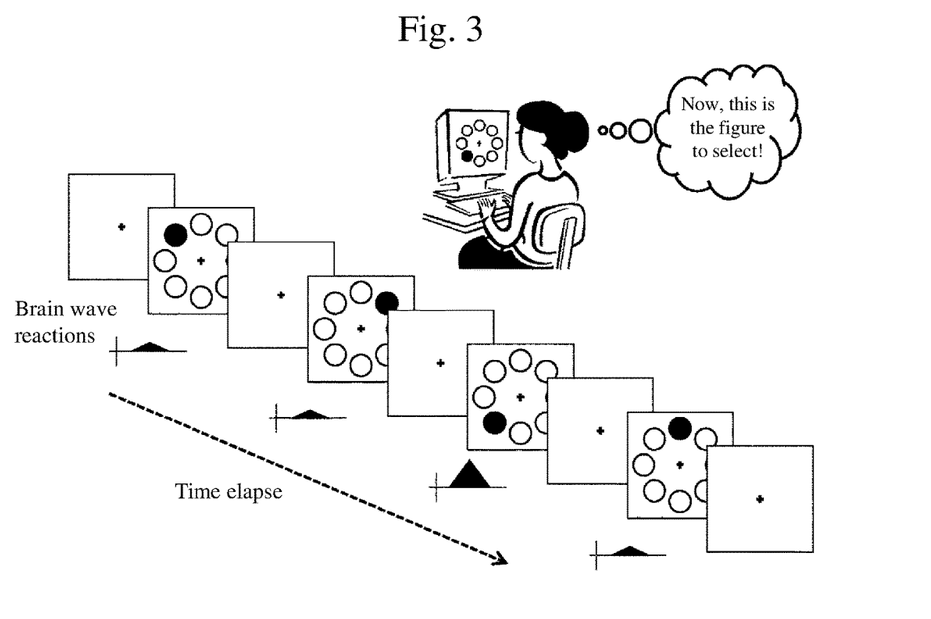
FIG. 3 illustrates an example of position discrimination in a personal identification behavioral task using brain waves according to the present embodiment.

FIG. 3 illustrates an example of position discrimination in a personal identification behavioral task using brain waves according to the present embodiment.

For increasing security level, the task is preferably implemented a plurality of times with different targets.

In both tasks, personal authentication is performed with reference to the index of whether the target among a plurality of visual stimuli that the user is trying to select in the mind can be decoded well from the brain waves. If the person has once been registered, decoding with high accuracy should be possible only when the model for the person is used, thus providing a proof for authentication.

Because even for the same user, the model required for decoding the brain waves differs between two kinds of tasks. Accordingly, by making it a condition that the decoding be successful with high accuracy in two types of tasks, security level can be increased. In particular, because figure discrimination and position discrimination have different brain activity contents, the models required for decoding the brain waves are different, so that using both in combination leads to an even higher security level.

In the personal authentication method according to the present invention, characteristic data of the individual brain waves for personal identification are registered in advance. That is, the personal authentication method of the present invention includes the step of "prior registration for personal identification".

First Embodiment

The present embodiment will be described with reference to the drawings.

Figure 4:
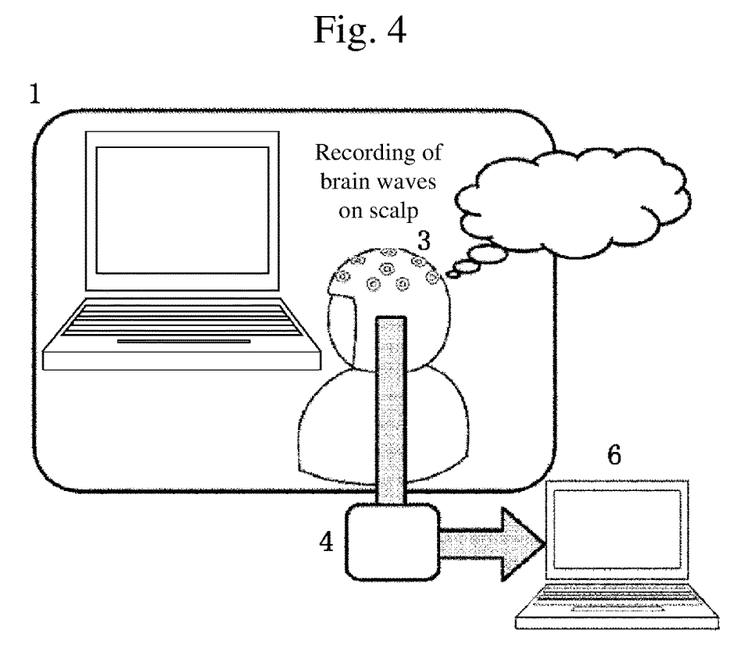
FIG. 4 is a schematic diagram of a device according to the present invention.

FIG. 4 schematically illustrates a device and method according to the present embodiment. As indicated by stimulus presentation 1 to a person as the object of personal authentication in FIG. 4, the person as the object of personal authentication is shown a display screen for stimulus presentation, and brain waves on the scalp of the person as the object of personal authentication are measured and recorded by an electroencephalograph (a brain wave amplifier 4 in the figure). The person as the object of personal authentication is fitted with electroencephalograph electrodes 3 for measuring brain waves. For example, the person wears a head cap to which the electroencephalograph electrodes are affixed. On a display screen (monitor), various visual stimuli are presented. The electroencephalograph acquires data of a raw waveform of the brain waves. The data of the brain wave raw waveform are analyzed and processed by a processing device such as a computer 6, and a determined result of personal authentication is displayed on the display screen and the like. In FIG. 4, the thick arrow extending from the head where the brain wave electrodes are positioned to the brain wave amplifier 4, and from the brain wave amplifier 4 to the computer 6, schematically indicates wired or wireless transmission of signals.

FIG. 2 schematically illustrates the presentation of stimulus events for figure discrimination, and the reaction thereto of the brain waves of the person as the object of personal authentication over time according to the present embodiment. As illustrated in FIG. 2, stimulus events (which may be referred to as attention-evoking events or test stimulus events), such as simple figures, are presented to the person as the object of personal authentication, one event (one sheet) at a time. The brain waves of the person as the object of personal authentication who saw the figures are measured, and the brain waves are analyzed using a brain wave analysis processing device, such as the computer. The stimulus events may include signs, illustrations, pictures, and photographs. This is a figure discrimination task common to prior registration and personal authentication steps, as will be described later.

Stimulus event presentation and the brain wave measurement with respect to the stimulus events (a) for prior registration will be specifically described.

One of a plurality of stimulus events, such as eight figures, is taught to the subject as the target. The subject is given a cognitive task of counting in the head the number of times the target appears among the stimulus events that are successively presented, and the associated brain waves are measured. The brain waves are measured from one or a plurality of electrodes attached to the scalp around the center of the top of the head. The measurement is performed according to a procedure indicated below. The electrodes are positioned at eight locations in accordance with a standard electrode placement system (10% system).

(1) The subject is presented with a plurality of visual stimuli (figures, illustrations, pictures, photograph, video and the like). For example, the visual stimuli (simple figures in FIG. 2) are successively presented on the computer display screen and the like, in a pseudo-random sequence, as in a picture-story show (see FIG. 2). The stimuli are not limited to visual stimuli, and may include auditory stimuli (sound, voice, music and the like), tactile stimuli, odor stimuli and the like.

(2) In this case, of the plurality of visual stimuli (a plurality of geometric figures in FIG. 2 (triangle, diamond, star shape, bi-elliptical shape, rectangle, circular shape, heart shape, clover shape and the like)), one (star shape, for example) is taught as the "target" to the person as the object of personal authentication. The person as the object of personal authentication is taught to perform a task of counting in the head the number of times the target stimulus is presented. A series of stimulus presentation including a specific visual stimulus as the target is referred to as a game. When a block comprises pseudo-random presentations of all of the visual stimuli (8 types), each once, each game comprises five blocks that are successively presented. In this case, each and every visual stimulus is presented five times. Each visual stimulus has a presentation time duration of 750 milliseconds each time. After an interval of 250 milliseconds, the next visual stimulus is presented.

(3) After a short rest, another game, i.e., the (2) is executed with the teaching of the target stimulus event changed. This is repeated until all of the plurality of visual stimuli are taught as the target. For example, when eight figures are used, a total of eight games are implemented. Between persons as the object of personal authentication, common targets are used.

The brain wave data illustrated in the bottom of FIG. 2 are an example of the brain wave data corresponding to the respective visual stimuli when the star shape is taught as the target and the subject is shown the visual stimuli and asked to count. As schematically illustrated, the brain wave data with respect to the visual stimulus of the target (star shape) show a greater reaction of the brain waves than the brain wave data with respect to the visual stimuli of the non-targets (triangle, diamond, and bi-elliptical shape). Similarly, when the other targets are taught, the brain wave data with respect to the target visual stimulus among the brain wave data in many cases show a greater reaction of the brain waves than the brain wave data with respect to the non-target stimuli.

The data acquired in the target selection task include a reaction immediately after the target presentation and a reaction immediately after a non-target presentation.

The brain waves with respect to the stimuli (visual stimuli, auditory stimuli, odor stimuli, tactile stimuli and the like) will be described. The present embodiment utilizes a brain wave potential referred to as an event-related potential (or event-related brain waves) with respect to a stimulus. Event-related potentials are transient brain waves which are produced in conjunction with the timing of occurrence of an external or internal event that affects a cognitive process, and include P300 (a positive potential change 300 milliseconds after stimulus presentation).

Brain wave data analysis processing and database registration (b) for prior registration will be specifically described.

With respect to the two types of tagged data, i.e., the brain wave data immediately after target presentation and the brain wave data immediately after non-target presentation, linear discrimination analysis is performed, and a discrimination model formula is generated. In the embodiment of the present invention, weighting coefficients of the model formula are optimized so as to produce an output such that the brain wave data for the target have a positive value, and the brain wave data for the non-target have a negative value.

The weighting coefficients of the discrimination model formula are stored in a storage unit of the device of the present embodiment for each individual and for each stimulus event. Similar data for a plurality of persons as the object of personal authentication are accumulated in the storage unit to create a database.

In the following, a discrimination score will be described in detail with reference to a mathematical expression. For example, a discrimination score (y) with respect to a single presentation of each visual stimulus is calculated using a linear discrimination function expressed by the following formula.

$$y = \sum_{i}^{n} w_i x_i + c \qquad \text{[Expression 1]}$$

In the expression of y, x is the value of brain wave data (voltage) of a certain channel at a certain point in time. The value x has types (n) corresponding to the product of the number of channels (the number of channels corresponding to the number of measurement locations because the brain wave data are obtained at a plurality of measurement locations on the scalp of the subject's head) and the data points. The weighting coefficient w with respect to the respective brain wave data and the constant term c can be determined by linear discrimination analysis.

Stimulus event presentation and brain wave measurement with respect to the stimulus events in step (A) of personal authentication will be specifically described.

Using the same stimulus types used in the above-described prior registration, and in the same way as described above with reference to (a) stimulus event presentation and brain wave measurement with respect to the stimulus events in prior registration, brain wave measurement is performed. That is, of a plurality of stimulus events, such as eight figures, one is taught as the target to the subject, and each subject is given the cognitive task of counting in the head the number of times the target appeared among the successively presented stimulus events, and the associated brain waves are measured.

During personal authentication, it is not necessary to set all of the plurality of stimulus types as the target. Neither is it necessary to implement all of the games if personal identification can be performed. A game may be interrupted when personal identification became possible.

Step (B) of personal authentication will be specifically described.

Using the discrimination model formulas of a plurality of persons registered in the database, quantification concerning "a likelihood of being the target" with respect to new brain wave data (brain wave data measured in a situation for authentication) for authentication purpose becomes possible. That is, in the present embodiment, with respect to each of the stimuli for the person to be authenticated (subject), a discrimination score is calculated using the discrimination model formulas of the plurality of registered persons registered in the database, and the scores are accumulated for each stimulus type.

When the stimulus type with the highest accumulated discrimination score obtained from the brain wave data of the subject in the final block matches the stimulus type set as the target, this is counted as a "successful decoding". Decoding accuracy is computed depending on how many of all of the games (eight games, for example) have been successfully decoded. The decoding accuracy varies between 0/8 to 8/8. Generally, the decoding accuracy increases as the number of times of repetition of stimulus presentation (the number of blocks) increases. However, even when the final results are the same, the decoding accuracy may be high from the beginning, or may increase halfway through, depending on the subject. Accordingly, the process of an increase in decoding accuracy corresponding to an increase in the number of blocks may be different. Thus, in a personal authentication system, it is preferable to use a block average of the decoding accuracy as detailed data of decoding accuracy.

Figure 5:
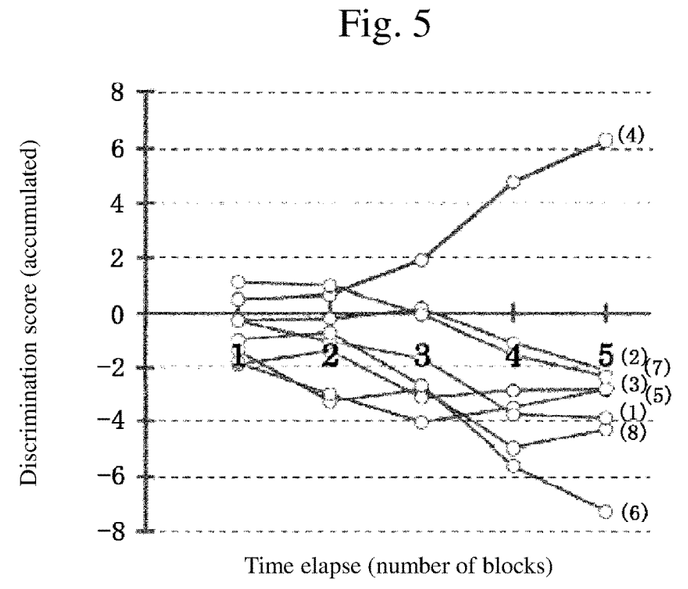
FIG. 5 illustrates transition of discrimination scores (accumulated) according to a first embodiment.

FIG. 5 is a graph illustrating the transition of discrimination scores in which, with respect to each of the stimuli ((1) to (8) in the figure) for a person to be authenticated (subject), a discrimination score is calculated using the discrimination model formula for each of a plurality of registered persons registered in the database, and the score is shown and accumulated for each stimulus type over a predetermined time elapsed. In FIG. 5, the vertical axis shows the accumulated discrimination score, and the horizontal axis shows the time elapsed by the number of blocks (first block to fifth block). It is seen that, as the discrimination score of the brain wave data for each stimulus in each block during the execution of the cognitive task of counting the target accumulates, the specific stimulus event (4) has the accumulated discrimination score of more than 6 in the fifth block accumulation, exhibiting the highest value. It is also seen that the accumulated discrimination scores for the other stimulus events (1), (2), (3), (5), . . . , and (8) are stably low as the blocks are accumulated.

Figure 6:
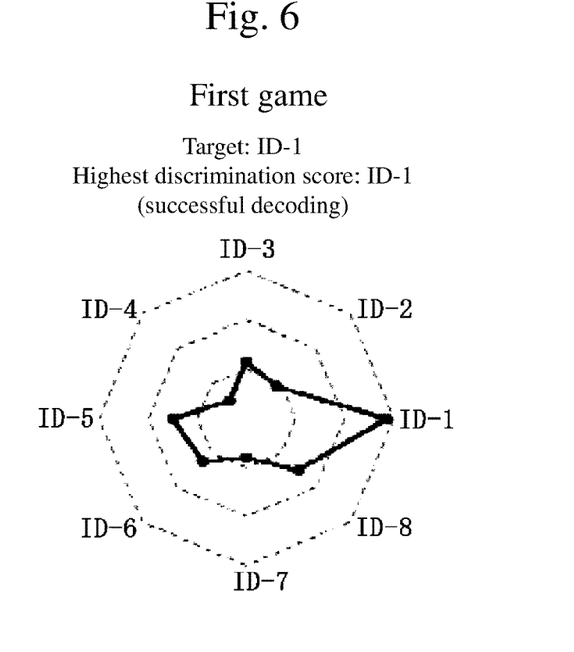
FIG. 6 illustrates an example of a first game according to the first embodiment.

FIG. 6 is a radar chart illustrating the discrimination scores of the eight stimulus events in the first game in which ID-1 (star shape figure, for example) was taught as being the target. In FIG. 6, the discrimination score for ID-1 is greater than the other discrimination scores and the highest. Accordingly, this is an example of successful decoding where the target taught and the stimulus event with the highest discrimination score are matched with each other.

Figure 7:
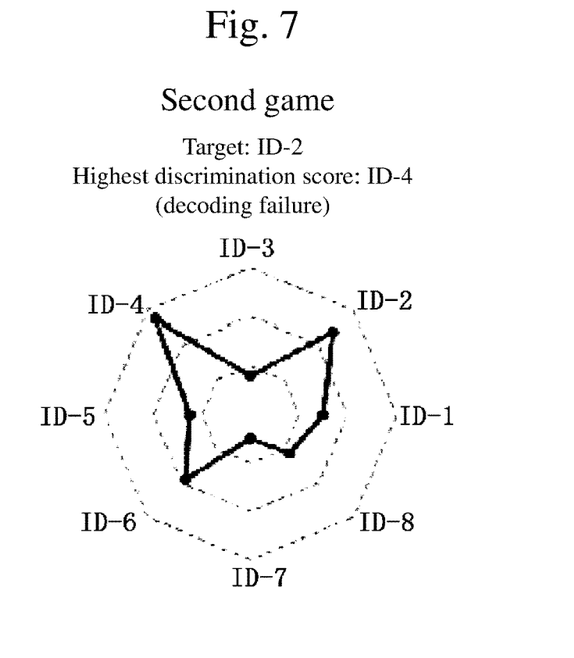
FIG. 7 illustrates an example of a second game according to the first embodiment.

FIG. 7 is a radar chart illustrating the discrimination scores of the eight stimulus events in the second game where ID-2 (triangle, for example) was taught as being the target. In FIG. 7, the discrimination score for ID-4 is greater than the other discrimination scores and the highest. Accordingly, this is an example of decoding failure where the target taught and the stimulus type with the highest discrimination score are not matched with each other.

In the present embodiment, decoding accuracy is determined by the numerical value obtained by dividing the number of successful decodings where the target taught and the stimulus type with the highest discrimination score are matched, by the total number (the sum of the number of decoding failures where the target taught and the stimulus type with the highest discrimination score are not matched, and the number of successful decodings). When eight stimulus events are used and the games are implemented using each and every one of the eight as the target taught, the decoding accuracy will be 0/8 to 8/8.

Figure 8:
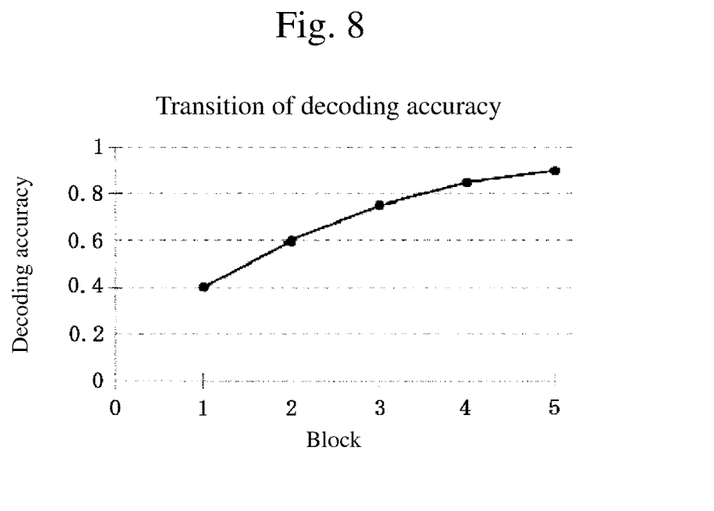
FIG. 8 illustrates transition of decoding accuracy according to the first embodiment.

FIG. 8 is an example of a graph showing the transition of decoding accuracy in the present embodiment. In FIG. 8, the vertical axis shows the decoding accuracy, and the horizontal axis shows the time elapsed by the number of blocks (first block to fifth block). FIG. 8 is an example of implementation in which the decoding accuracy is calculated from the accumulated discrimination score. It is also possible to calculate the decoding accuracy from the discrimination score of brain wave data for each block during the execution of the cognitive task of counting the target. From the accumulated discrimination score of brain wave data when the game has been implemented up to a particular block, the decoding accuracy in that block may be calculated. As a technique for expression in numerical terms, including the transition of decoding accuracy, the curve of decoding accuracy may be integrated to provide a numerical value. In the first to the third embodiments, the value is used as an index for comparison between discrimination models.

As illustrated in FIG. 8, generally, as the number of blocks increases, the decoding accuracy increases.

While the example involving eight stimulus types and five blocks has been described, the number of blocks may be set as appropriate in the brain wave measurement for authentication. With respect to the brain wave data for each stimulus for the person to be authenticated, the discrimination score is calculated using the discrimination model formula for each of a plurality of registered persons registered in the database, and then the discrimination score is accumulated for each stimulus type over a predetermined time elapsed (a number of blocks). When the stimulus type of which the accumulated discrimination score obtained from the brain wave data of the subject in each block became the highest is matched with the stimulus type set as the target, this is counted as a successful decoding. Then, decoding accuracy is computed depending on how many of all of the games (eight games, for example) resulted in successful decoding.

Identification of the person who provided the model with the highest decoding accuracy in step (C) of personal authentication will be specifically described.

The registered person who provided the discrimination model formula with the highest decoding accuracy among the decoding accuracies obtained in step (B) is identified. Authentication is performed to prove that the person to be authenticated is the registered person identified among authentication candidates who are registered in advance.

The authentication may be performed by asking the person to be authenticated to input the ID, such as letters of the alphabet or numbers, of the object candidate registered in advance, and by determining whether the ID matches the registered person identified as having the highest decoding accuracy.

In order to further increase the reliability of authentication, a known authentication method, such as fingerprint authentication, may be used in combination.

While the embodiment has been described mainly with reference to visual stimuli, the stimuli may comprise auditory stimuli, tactile stimuli, odor stimuli and the like instead of visual stimuli, and the corresponding brain waves may be measured and analyzed.

Second Embodiment

The first embodiment has been described with reference to the example in which, as illustrated in FIG. 2, the behavioral task for personal identification by brain waves involved figure discrimination. In the present embodiment, as illustrated in FIG. 3, position discrimination is used as a behavioral task for personal identification by brain waves. The present embodiment is similar to the first embodiment with the exception that visual stimuli concerning position discrimination is handled.

In the target selection task concerning position discrimination, any of a plurality of positions on the screen (eight locations in the example) is randomly flashed, where one of the positions is the target. The position discrimination selection task is also implemented a plurality of times with the target position varied. When the behavioral task involves figure discrimination and when it involves position discrimination, the cognitive function of the brain is different. Position discrimination, as opposed to the discrimination of different figures or pictures, can be performed by the brain at high speed. Accordingly, faster authentication can be expected.

Figure 9:
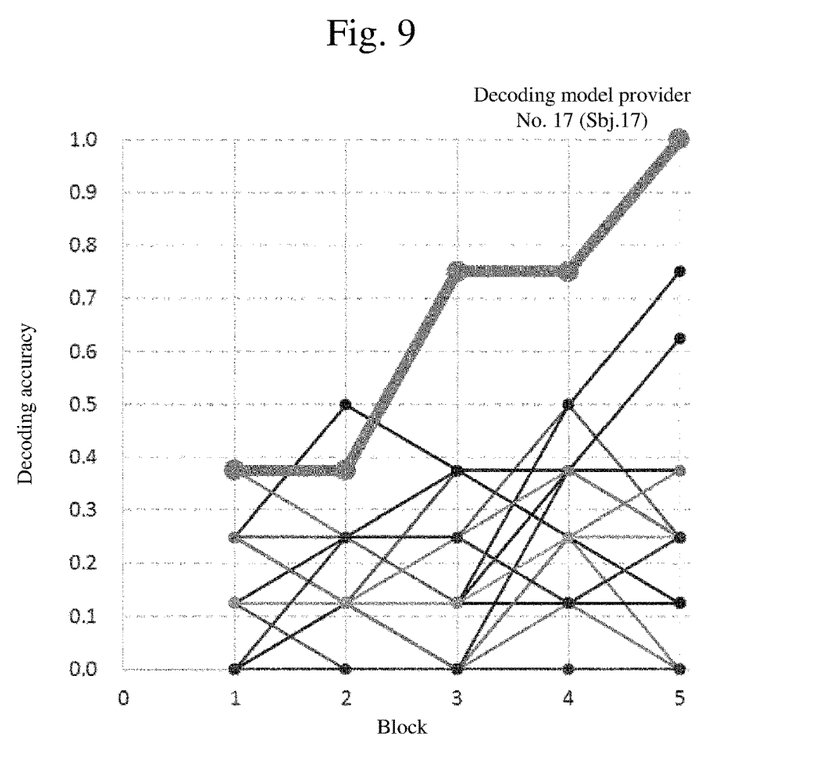
FIG. 9 illustrates transition of decoding accuracy in an example of personal authentication according to a second embodiment.
Figure 10:
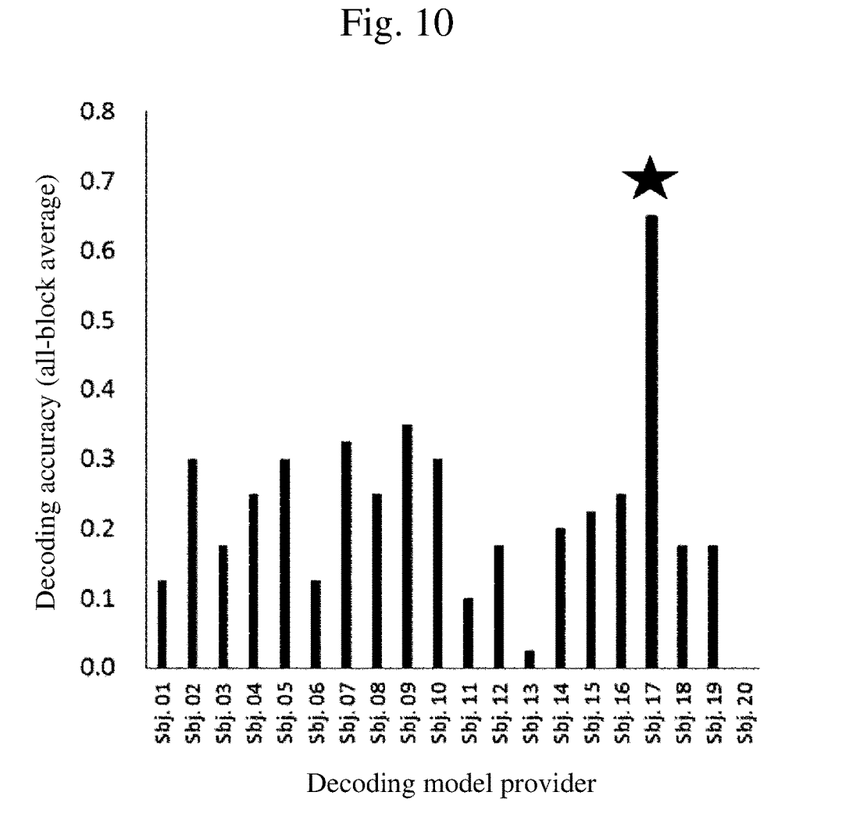
FIG. 10 illustrates the results of personal authentication in an example of personal authentication according to the second embodiment.

FIGS. 9 and 10 illustrate examples of the results of an experiment of personal authentication by brain waves. The experiment was implemented with a target task concerning position discrimination. For each of subjects who were authentication candidates, a cognitive task was implemented in which eight visual stimuli, differing only in the position where they flashed, were successively presented, and the subject counted the number of times one of the visual stimuli which had been taught to be the target, followed by the measurement of the corresponding brain waves. During the prior registration for registering a discrimination model formula in advance, the discrimination model formula was generated using data from eight games of 15 blocks. Then, in the step of personal authentication with respect to the person to be authenticated, an experiment of eight games of five blocks was performed under the same conditions as in the prior registration. Then, with respect to the obtained brain wave data of the person to be authenticated, decoding accuracy was determined by applying the discrimination model formula of each of the candidate object persons ("Discrimination model provider" in the figures) who had been prior-registered earlier. FIG. 9 illustrates how the decoding accuracy determined by applying the discrimination model formulas of the candidate object persons transitions as the blocks accumulated. It is seen that the decoding accuracy value is the highest when the discrimination model formula of the candidate object person No. 17 was applied compared with when the discrimination model formulas of the other candidate object persons were applied. The transition of the decoding accuracy shows that, as the number of blocks increases and the decoding accuracy accumulates, the decoding accuracy becomes the highest in the case of No. 17 when three or more blocks are accumulated. FIG. 10 illustrates the decoding accuracy with respect to the discrimination model providers No. 1 to No. 20 based on the results of FIG. 9, in all-block average. From the results of the experiment, it is seen that the highest decoding accuracy with respect to the brain wave data of the subject No. 17 (Sbj. 17) corresponds to the discrimination model of the subject. As a result of similar experiments conducted with respect to authentication experiments for 20 persons, a similar phenomenon was confirmed with respect to the data of 19 subjects. This corresponded to the authentication accuracy of 95%, which is higher than the accuracy of authentication using conventional brain wave data. When one person who could not be authenticated was analyzed, the person was second only to the candidate object person with the highest decoding accuracy. Accordingly, it is possible to attain 100% authentication accuracy by increasing the number of blocks, for example.

Third Embodiment

The first and the second embodiments have been described with reference to the examples in which the behavioral tasks for personal identification by brain waves included figure discrimination and position discrimination. In the present embodiment, with respect to both a figure discrimination task and a position discrimination task, prior registration of a discrimination model formula and personal authentication are performed. During personal authentication, if a difference in decoding accuracy from the second place and below is caused in the first task, the other task may not be implemented. In this way, one of the figure discrimination task and the position discrimination task may be omitted as appropriate.

Fourth Embodiment

In the first to the third embodiments, personal authentication has been described focusing on decoding accuracy. In the present embodiment, instead of decoding accuracy, personal authentication is performed focusing on the discrimination score itself that is calculated when determining decoding accuracy. As illustrated in FIG. 5, the discrimination scores (accumulated) are calculated on the stimulus type unit basis. This is utilized in the present embodiment, where authentication is performed by comparing the value of the discrimination score according to each stimulus type or the value of the accumulated discrimination score between a plurality of discrimination models of a plurality of authentication candidates.

In the following, the present embodiment will be specifically described in which a single decoding trial comprises a game in which a target is taught once in a target stimulus task (one gage according to the first embodiment). The brain waves of a person to be authenticated who is wishing for authentication are measured. With respect to the brain wave data, using the discrimination model of each of a plurality of registered persons registered in the database, an accumulated discrimination score for all of the blocks is calculated for each stimulus type in each decoding trial in which a specific stimulus type becomes the target. The resultant accumulated discrimination scores for the stimulus types are standardized such that the average value is 0 and the standard deviation is 1, thereby calculating a standard accumulated discrimination score. This computation is performed for all of the decoding trials, and then an average value of the standard accumulated discrimination score with respect to the target is determined. This operation is performed for each of the discrimination models registered in the database. Based on the result, the person who provided the discrimination model of which the standard accumulated discrimination score with respect to the target is the highest is estimated and authenticated to be that person.

In another specific example, authentication may be performed by ranking the accumulated discrimination scores in descending order of scores in each decoding trial, and comparing average values of the ranking data with respect to all of the decoding trials to provide the discrimination model with the highest rank (1st place).

In the case of the present embodiment, the authentication operation can be performed with a decoding trial using a single stimulus type or some of the stimulus types as the target, rather than performing the decoding trial using all of the stimulus types as the target. The method by which, with respect to the decoding trials in which each of the maximum of eight types of stimuli is made the target (eight decoding trials), the standard accumulated discrimination scores are determined, and their average value is used to determine the most suitable discrimination model can provide higher authentication accuracy. It is also possible to decrease the number of blocks, i.e., the number of times a stimulus group is repeated, and authentication is possible when there is at least one block (eight types of stimuli, including the target, are presented, each once).

Further, in the first to the third embodiments, too, it is possible to perform authentication by determining averages of a ranking of averages of the transition of decoding accuracy in descending order of the averages and a ranking of the accumulated discrimination scores in descending order of the scores to determine the highest rank (1st place).

In the first to the fourth embodiments, the authentication methods have been presented that focused on the brain waves to identify who the person to be authenticated is, assuming that the person is one of the persons registered in the database. However, in an actual situation for authentication, a person who is not registered in the database may be the object of authentication. In this case, it is contemplated to be effective, as a technique for eliminating un-registered persons, to focus on decoding accuracy. That is, if the person to be authenticated is one of the persons registered in the database, the decoding accuracy of the cognitive task should become very high when his or her own model is used (90% or more, from the knowledge gained in the past). Accordingly, even when a threshold value of decoding accuracy is set at 0.7 (70%), for example, a negative determination can be made, i.e., it can be determined that the person is not registered in the database if the decoding accuracy is below the threshold value. If the threshold value is made too low, the risk of authenticating a person not registered in the database as one of the registered persons increases. Conversely, if the threshold value is set too high, the risk of wrongly rejecting a person registered in the database as being a non-registered person increases. Accordingly, the setting of the threshold value should be made depending on which of the risks is more desirable to be eliminated. As a technique for authentication/rejection by the threshold value setting, the accumulated discrimination score (its average value) with respect to the target may be used as an index, instead of decoding accuracy. It is also possible to set the threshold value using both the index and decoding accuracy.

The examples described with reference to the embodiments and the like have been described for facilitating an understanding of the invention, and the present invention is not limited to such embodiments.

REFERENCE SIGNS LIST

1 Stimulus presentation to a subject
3 Electroencephalograph electrodes on the subject
4 Brain wave amplifier
6 Computer

The invention claimed is:

1. An authentication device using brain waves, the device comprising:
   an electroencephalograph; and
   a processing unit which, with respect to brain waves obtained by the electroencephalograph with respect to a plurality of static imagery stimulus events, determines a discrimination score according to a discrimination model for estimating brain information for each authentication candidate accumulated in advance, and which, based on a discrimination-model-to-discrimination-model comparison of the discrimination score, identifies and authenticates an authentication candidate who provided the model.

2. The authentication device using brain waves according to claim 1, wherein the identifying of the authentication candidate based on the discrimination-model-to-discrimination-model comparison in the processing unit is based on the discrimination score and/or a decoding accuracy determined from the discrimination score.

3. The authentication device using brain waves according to claim 1, wherein the brain waves are brain waves related to a cognitive process with respect to the stimulus events.

4. The authentication device using brain waves according to claim 1, wherein the discrimination model for estimating the brain information has a weighting coefficient therefor optimized so as to enable decoding of a target from the brain waves in a target selection task.

5. The authentication device using brain waves according to claim 1, further comprising a stimulus presentation unit which presents a plurality of stimulus events, and a target presentation unit which indicates which of the plurality of stimulus events is a target,
   wherein the brain waves obtained by the electroencephalograph are brain waves related to a cognitive task for selecting the target.

6. The authentication device using brain waves according to claim 5, wherein the stimulus presentation unit presents stimulus events having different figures, or stimulus events which only differ in position.

7. The authentication device using brain waves according to claim 1, wherein the identifying of the authentication candidate based on the discrimination-model-to-discrimination-model comparison by the processing unit comprises identifying a highest rank by: a rank, by the discrimination-model-to-discrimination-model comparison, of an average value with respect to a target in standardized data of an accumulated discrimination score with respect to each stimulus type; a rank, by the discrimination-model-to-discrimination-model comparison, of a decoding accuracy determined from the discrimination score; or an average value of ranks of accumulated values of both the discrimination score and the decoding accuracy.

8. An authentication device using brain waves, the device comprising:
   an electroencephalograph; and
   a processing unit which determines decoding accuracy by subjecting brain waves obtained by the electroencephalograph with respect to a plurality of static imagery stimulus events to decoding processing according to a decoding model for estimating brain information for each authentication candidate accumulated in advance, and identifies and authenticates an authentication candidate who provided the model formula, based on the decoding accuracy.

9. An authentication method using brain waves, the method comprising:
   measuring brain waves of a person to be authenticated which are caused by a plurality of static imagery stimulus events;
   determining, with respect to the brain waves, a discrimination score according to a discrimination model for estimating brain information for each authentication candidate accumulated in advance; and
   based on a discrimination-model-to-discrimination-model comparison of the discrimination score, identifying and authenticating an authentication candidate who provided the discrimination model.

10. An authentication system using brain waves, the system comprising a stimulus presentation device, an electroencephalograph, and a processing device which processes brain wave data from the electroencephalograph,
   wherein:
   the stimulus presentation device presents a plurality of static imagery stimulus events including a target and a non-target, each a plurality of times;
   the electroencephalograph measures the brain waves of a person to be authenticated which are caused by the plurality of static imagery stimulus events; and
   the processing device, with respect to the brain waves, determines a discrimination score according to a discrimination model for estimating brain information for each authentication candidate accumulated in advance, and, based on the discrimination score, identifies and authenticates an authentication candidate who provided the model.

11. A non-transitory computer-readable medium program for causing a computer to function as:
   a stimulus presentation means which presents a plurality of static imagery stimulus events, each a plurality of times;
   a processing means which, with respect to brain wave data immediately after the stimulus presentation, determines a discrimination score according to a discrimination model for estimating brain information for each authentication candidate accumulated in advance, and, based on the discrimination score, identifies and authenticates an authentication candidate who provided the model; and
   a presenting means which presents an authentication result.

* * * * *